United States Patent
Hoheisel

(10) Patent No.: US 7,039,160 B2
(45) Date of Patent: May 2, 2006

(54) APPARATUS AND METHOD FOR GENERATING MONOCHROMATIC X-RAY RADIATION

(75) Inventor: Martin Hoheisel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 93 days.

(21) Appl. No.: 10/637,912

(22) Filed: Aug. 8, 2003

(65) Prior Publication Data
US 2004/0131153 A1    Jul. 8, 2004

(30) Foreign Application Priority Data
Aug. 9, 2002   (DE)   ................. 102 36 640

(51) Int. Cl.
*G21K 1/06*    (2006.01)
(52) U.S. Cl. .................................... 378/84
(58) Field of Classification Search ............ 378/82–85
See application file for complete search history.

(56) References Cited
U.S. PATENT DOCUMENTS
5,596,620 A * 1/1997 Canistraro et al. ............ 378/84
5,757,882 A * 5/1998 Gutman ........................ 378/84
2003/0112923 A1   6/2003 Lange et al.

FOREIGN PATENT DOCUMENTS
DE    199 55 848    5/2000

\* cited by examiner

*Primary Examiner*—Craig E. Church
(74) *Attorney, Agent, or Firm*—Schiff Hardin LLP

(57) ABSTRACT

In an apparatus and a method for generating monochromatic X-ray radiation, an X-ray source, a monochromator and a slit collimator are arranged relative to one another such that X-rays of a specific energy among the X-rays emanating from the X-ray source are reflected at the monochromator and emerge through the slit of the slit collimator as a fan-shaped beam of monochromatic X-radiation. For scanning an examination subject with the X-ray beam, the monochromator is adjustable relative to the X-ray source and the slit collimator such that the condition for the reflection angle required for the reflection of X-rays of the specific energy at the monochromator remains substantially satisfied during the adjustment, and essentially only X-rays of the specific energy pass through the slit of the slit collimator.

18 Claims, 2 Drawing Sheets

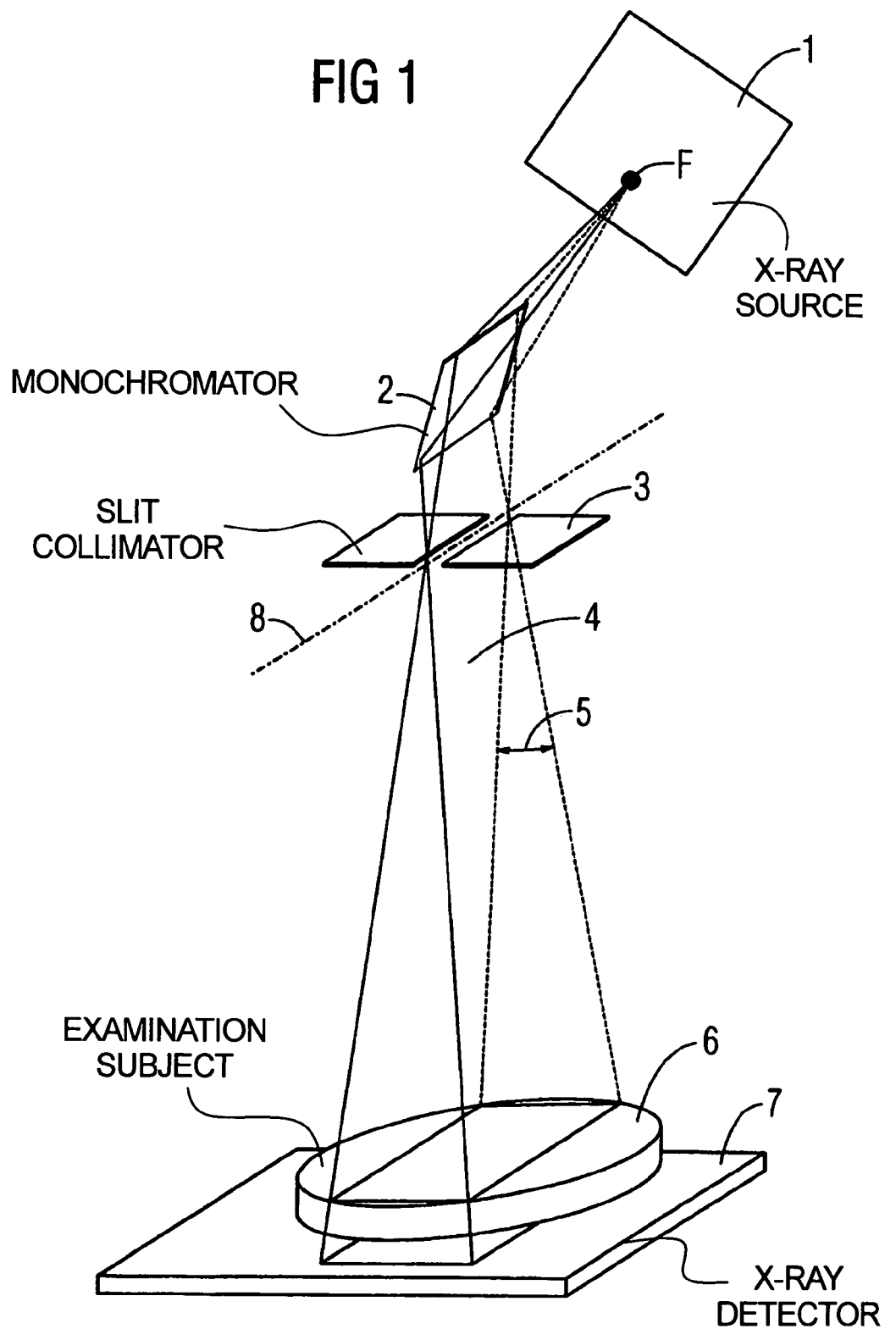

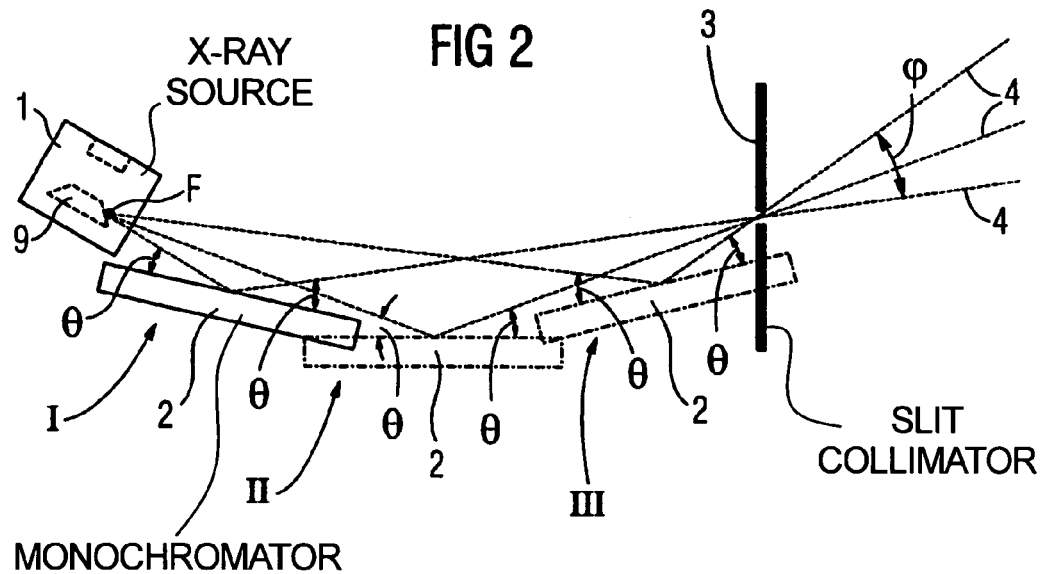
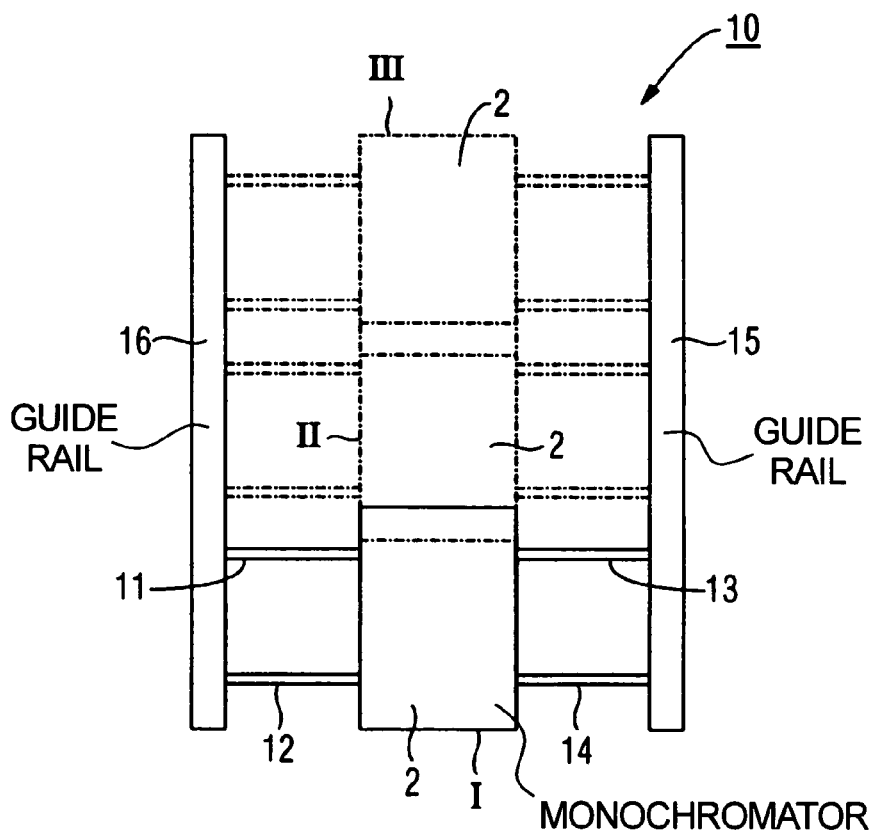

APPARATUS AND METHOD FOR GENERATING MONOCHROMATIC X-RAY RADIATION

BACKGROUND OF THE INVENTION

1. Field of the Invention

The present invention is directed to an apparatus and a method for generating monochromatic X-ray radiation, of the type using an X-ray source, a monochromator and a slit collimator that are arranged relative to one another so that X-rays of a specific energy among the X-rays emanating from the X-ray source are reflected at the monochromator and emerge through the slit of the slit collimator.

2. Description of the Prior Art

Monochromatic X-ray radiation is especially desired particularly in some areas of medical technology, for example in mammography, since it enables the imaging of body details with higher contrast than polychromatic radiation, with which parts of the X-ray spectrum are always absorbed in the patient under examination, thereby increasing the radiation dose for the patient without contributing to the image. A reduction of the dose for the patient therefore can be achieved with monochromatic radiation.

Also, by a designational utilization of monochromatic X-ray radiation at a specific energy, materials such as contrast agents in medical technology are especially well emphasized in an X-ray image. When, for example, iodine is employed as a contrast agent that is injected into the body of a patient, monochromatic radiation with an energy of approximately 33 keV should be employed so that the tissue structures having the iodine appear especially clearly in generated X-ray images.

An apparatus and a method for generating monochromatic X-ray radiation are disclosed in German OS 199 55 848. As can be seen from FIG. 1 herein, which shows an apparatus according to German OS 199 55 848, the apparatus has an X-ray source 1 (merely indicated here), a monochromator 2 as well as a slit collimator 3. The monochromator 2 is arranged at an angle—referred to as the Bragg angle—relative to the focus F of the X-ray source 1 so that only X-rays with a specific energy are reflected at the monochromator 2 at this angle. These X-rays subsequently pass through the slit of the slit collimator 3 and form a fan-shaped, monochromatic X-ray beam 4 having an aperture angle 5. After penetrating an examination subject 6, the X-ray beam 4 is incident on an X-ray detector 7.

Since the aperture angle 5 usually amounts to only approximately 1°, the X-ray source 1, the monochromator 2 as well as the slit collimator 3 must be rotated around an axis 8 intersecting the slit collimator 3 in order to scan the examination subject 6 with the fan-shaped, monochromatic X-ray beam 4 and acquire a planar X-ray image of the examination subject 6. It is disadvantageous that comparatively long exposure times are required.

SUMMARY OF THE INVENTION

An object of the present invention is to provide an apparatus and a method of the type initially described with which the production of an X-ray image of an examination subject with monochromatic X-ray radiation is simplified.

According to the invention, this object is achieved by an apparatus and a method wherein an X-ray source, a monochromator and a slit collimator are arranged at an angle relative to one another such that only X-rays of a specific energy among the X-rays emanating from the X-ray source are reflected at this angle at the monochromator and emerge through the slit of the slit collimator, and for scanning an examination subject to be charged with monochromatic X-rays, the monochromator is adjustable relative to the X-ray source and the slit collimator on a predefined path such that the condition for the reflection angle required for the reflection of X-rays remains substantially satisfied during the adjustment and essentially only X-rays of the specific energy pass through the slit of the slit collimator. The monochromator is thus adjusted relative to the X-ray source and the slit collimator so that only X-rays of a specific energy proceed through the slit of the slit collimator, so an angular range, and thus an examination subject, can be scanned with the generated, fan-shaped monochromatic X-ray beam due to the adjustment of the monochromator relative to the slit collimator. In this way, an X-ray exposure of an examination subject can be acquired relatively simply with monochromatic X-ray radiation.

In versions of the invention the monochromator is a monochromator crystal, preferably a highly oriented, pyrolytic graphite crystal, referred to as an HOPG crystal. When X-ray radiation emitted by the X-ray source strikes such an HOPG crystal at the Bragg angle (the Bragg angle for a photon energy of, for example, 17 keV amounts to 6.1°) the HOPG crystal reflects monochromatic X-ray radiation of this energy at this angle in the direction toward the slit of the slit collimator. A fan-shaped beam of monochromatic X-rays ultimately passes through the slit collimator.

According to another version of the invention, the monochromator can be a multi-layer system, for example Göbel mirrors, that reflects X-rays.

In further versions of the invention the monochromator is adjustable along a substantially elliptical path, and the focus of the X-ray source in a preferred embodiment located substantially in one focus of the ellipse defining the elliptical path, and the slit of the slit collimator is substantially located in the other focus of the ellipse. As a result of the adjustment of the monochromator on an elliptical path, the Bragg condition for the reflection of X-rays of a specific energy remains essentially met. However, the reflected, monochromatic X-radiation passes through the slit of the slit collimator at various angles, so the scan effect is achieved.

DESCRIPTION OF THE DRAWINGS

FIG. 1 shows a structure of an apparatus for generating monochromatic X-radiation according to the Prior Art.

FIG. 2 shows the basic structure of an apparatus for generating monochromatic X-radiation according to the invention.

FIG. 3 is a top view of an adjustment mechanism for the monochromator shown in FIG. 2.

DESCRIPTION OF THE PREFERRED EMBODIMENTS

The present invention is a modification of the method and apparatus that were initially described and is shown in FIG. 1. X-rays emanating from the focus F of the schematically indicated X-ray source 1 strike the monochromator 2, at which they are diffracted and reflected. X-rays of a specific energy are selectively reflected at a specific angle at the monochromator 2. The slit collimator 2 is arranged such relative to the monochromator 2 and the X-ray source 1 so that only X-rays of this specific energy can pass through the slit of the slit collimator 3 and form a fan-shaped beam 4 of monochromatic X-rays having an aperture angle 5. After the monochromatic X-ray beam 4 has penetrated through an examination subject 6, it strikes an X-ray detector 7. Since, as already mentioned, the aperture angle 5 only amounts to approximately 1°, only a small strip of the examination subject 6 is penetrated by the monochromatic X-ray beam 4. For generating a planar X-ray image of the examination subject 6, the apparatus composed of the X-ray source 1, monochromator 2 and slit collimator 3 must be rotated around the axis 8 shown in FIG. 1.

In order to avoid this rotation around the axis 8, which involves a relatively long exposure time for acquiring a planar X-ray exposure of the examination subject 6, in accordance with the invention the monochromator 2 is adjusted relative to the X-ray source 1, or the focus F of the X-ray source 1, and relative to the slit collimator 3 in order to acquire a planar X-ray exposure of the examination subject 6, as shown in FIG. 2. As an example, FIG. 2 shows three positions I, II and III of the monochromator 2 relative to the focus F of the X-ray source 1 and relative to the slut collimator 3. The adjustment of the monochromator 2 relative to the X-ray source 1 and the slit collimator 3 ensues such that the condition for the reflection angle Θ required for the reflection of X-rays of a specific energy at the monochromator 2 remains substantially satisfied during the entire adjustment motion of the monochromator 2 relative to the X-ray source 1 and the slit collimator 3, and thus substantially only X-rays of the specific energy can pass through the slit of the slit collimator 3. As shown in FIG. 2 for the three positions I, II and III of the monochromator 2, the X-ray beam emanating from the focus F of the X-ray source 1 strikes the monochromator 2 at the angle Θ, and X-rays of a specific energy are reflected at the angle Θ at the monochromator 2 and pass through the slit of the slit collimator 3 as a fan-shaped beam 4 of monochromatic X-radiation. When, accordingly, the monochromator 2 is continuously adjusted from its initial position I shown in FIG. 2 into its final position III shown in FIG. 2 during the acquisition of an X-ray exposure of the examination subject 6, then the fan-shaped, monochromatic X-ray beam 4 sweeps an angular range φ that suffices in order to scan the examination subject 6.

When, for example, the apparatus for generating monochromatic X-radiation is provided for employment in mammography, then an X-ray source 1 that has an anode 9 of molybdenum is usually employed. In this case, the monochromator 2 is arranged or adjustable such relative to the focus F of the X-ray source 1 and the slit of the slit collimator 3 such that a reflection angle Θ of the X-ray radiation (Bragg angle) is adhered to at which X-ray radiation having an energy of approximately 17.5 keV is selected, this corresponding to the energy of the $K_\alpha$ line of molybdenum. Given this arrangement, essentially only X-rays of this energy pass through the slit of the slit collimator 3, which preferably has a width of approximately 50 µm. The monochromator 2 is a monochromator crystal, preferably an HOPG crystal (highly oriented pyrolytic graphite crystal).

As indicated in FIG. 2, the HOPG crystal 2 is preferably adjusted along an elliptical path, with the focus F of the X-ray source 1 situated in one focus of the ellipse defining the elliptical path and the slit of the slit collimator 3 situated in the other focus of the ellipse. The duration of the adjustment motion of the HOPG crystal 2 from its initial position I into its final position III essentially corresponds to the duration for the acquisition of a planar X-ray exposure or to a whole-numbered fraction of this duration.

When, for example, the distance of the slit of the slit collimator 3 from the focus F of the X-ray source 1 amounts to 10 cm and the HOPG crystal 2 is moved from its initial position I, in which it is situated approximately 1 cm in front of the focus F of the X-ray source 1, into its final position III wherein it is situated approximately 1 cm in front of the slit of the slit collimator 3, then an exit angle range φ of approximately 12.8° occurs given a Bragg angle of Θ=8°. Given a distance of 80 cm of the slit of the slit collimator 3 from the plane of the X-ray detector 7, thus, a region of 18 cm can be swept on the X-ray detector 7. This corresponds to the standard X-ray film width.

FIG. 3 shows a schematic top view of an adjustment mechanism 10 for the HOPG crystal 2. In the exemplary embodiment shown in FIG. 3, the HOPG crystal 2 is provided with four rods 11 through 14 that are guided in guide rails 15 and 16 at both sides of the monochromator 2. The adjustment of the rods 11 through 14 in the guide rails 15 through 16 ensues electromotively (in a way that is not shown). The adjustment is controlled by a conventional computer device that is not shown and that is suitably programmed for the aforementioned control.

Compared to the known method and apparatus initially described, the inventive apparatus and method have the advantages that an examination subject can be scanned with a fan-shaped beam of monochromatic X-radiation in a comparatively short time using a less complex apparatus. Planar detectors, for example X-ray films, X-ray image intensifiers or solid-state detectors can be employed.

As an alternative to HOPG crystals, other monochromator crystals or multi-layer systems, for example Göbel mirrors, that reflect X-rays can be employed as the monochromator.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for generating monochromatic x-ray radiation comprising:

an x-ray source which emits x-rays from a focus, a monochromator, and a slit collimator disposed in succession relative to each other, with said focus said x-ray source and the slit of said collimator in a fixed positional relation to each other, so that x-rays of a specific energy among the x-rays emitted by the x-ray source are reflected at the monochromator and subsequently pass through the slit of the slit collimator, and an adjustment mechanism connected to said monochromator for displacing only said monochromator relative to both said x-ray source and said slit collimator while emitting x-rays from said x-ray source and while substantially maintaining a reflection angle for reflection of said x-rays of said specific energy at said monochromator, for correspondingly displacing an x-ray beam emerging from said slit of said slit collimator through a scanning angle range.

2. An apparatus as claimed in claim 1 wherein said monochromator is a monochromator crystal.

3. An apparatus as claimed in claim 1 wherein said monochromator is a highly oriented pyrolytic graphite crystal.

4. An apparatus as claimed in claim 1 wherein said monochromator is a multi-layer system that reflects said x-rays.

5. An apparatus as claimed in claim 4 wherein said monochromator is a Göbel mirror.

6. An apparatus as claimed in claim 1 wherein said adjustment mechanism displaces said monochromator along a substantially elliptical path.

7. An apparatus as claimed in claim 6 wherein said focus of said x-ray source is disposed substantially at one focus of an ellipse defining said elliptical path, and wherein said slit of said slit collimator is situated substantially in the other focus of said ellipse.

8. An apparatus as claimed in claim 1 wherein said scanning beam is used for conducting an x-ray exposure having a duration, and wherein said adjustment mechanism displaces said monochromator along a displacement path for a duration substantially corresponding to said duration of said x-ray exposure.

9. An apparatus as claimed in claim 1 wherein said scanning beam is used for conducting an x-ray exposure having a duration, and wherein said adjustment mechanism displaces said monochromator along a displacement path for a duration substantially corresponding to a whole-number fraction of said duration of said x-ray exposure.

10. A method for generating monochromatic x-ray radiation comprising:
    arranging an x-ray source which emits x-rays from a focus, a monochromator, and a slit collimator in succession relative to each other so that x-rays of a specific energy among the x-rays emitted by the x-ray source are reflected at the monochromator and subsequently pass through the slit of the slit collimator; and
    while emitting x-rays from said x-ray source, displacing only said monochromator relative to both said x-ray source and said slit collimator, while maintaining said focus at said x-ray source and the slit of said collimator in a fixed positional relation to each other and while substantially maintaining a reflection angle for reflection of said x-rays of said specific energy at said monochromator, for correspondingly displacing an x-ray beam emerging from said slit of said slit collimator through a scanning angle range.

11. A method as claimed in claim 10 comprising employing a monochromator crystal as said monochromator.

12. A method as claimed in claim 10 comprising employing a highly oriented pyrolytic graphite crystal as said monochromator.

13. A method as claimed in claim 10 comprising employing a multi-layer system that reflects said x-rays as said monochromator.

14. A method as claimed in claim 13 comprising employing a Göbel mirror as said monochromator.

15. A method as claimed in claim 10 comprising displacing said monochromator along a substantially elliptical path.

16. A method as claimed in claim 15 comprising disposing said focus of said x-ray source substantially at one focus of an ellipse defining said elliptical path, and situating said slit of said slit collimator is substantially in the other focus of said ellipse.

17. A method as claimed in claim 10 comprising conducting an x-ray exposure, with said scanning beam, having a duration, and displacing said monochromator along a displacement path for a duration substantially corresponding to said duration of said x-ray exposure.

18. A method as claimed in claim 10 comprising conducting an x-ray exposure, with said scanning beam, having a duration, and displacing said monochromator along a displacement path for a duration substantially corresponding to a whole-number fraction of said duration of said x-ray exposure.

* * * * *